(12) United States Patent
Aeschbach

(10) Patent No.: US 8,546,761 B2
(45) Date of Patent: Oct. 1, 2013

(54) BELLOWS ACTUATED INFRARED (IR) STAGE

(75) Inventor: James Aeschbach, Cross Plains, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 40 days.

(21) Appl. No.: 13/436,559

(22) Filed: Mar. 30, 2012

(65) Prior Publication Data

US 2012/0262710 A1  Oct. 18, 2012

Related U.S. Application Data

(60) Provisional application No. 61/475,545, filed on Apr. 14, 2011.

(51) Int. Cl.
*G02B 21/26* (2006.01)
*G01N 21/00* (2006.01)
*G01N 21/35* (2006.01)

(52) U.S. Cl.
USPC .............. 250/339.11; 250/341.8; 250/339.07; 359/391; 356/244; 356/440

(58) Field of Classification Search
USPC ............ 250/339.11, 341.8, 339.07; 359/391; 356/244, 440
See application file for complete search history.

(56) References Cited

U.S. PATENT DOCUMENTS

| 4,303,859 | A | 12/1981 | McCue |
| 5,075,551 | A | 12/1991 | Watanabe |
| 5,506,416 | A * | 4/1996 | Rizvi ........................ 250/339.06 |
| 5,693,345 | A | 12/1997 | Chen et al. |
| 7,935,929 | B2 * | 5/2011 | Hoult et al. .............. 250/339.07 |
| 8,223,430 | B2 * | 7/2012 | Hoult et al. ................... 359/391 |
| 2008/0285122 | A1 | 11/2008 | Hoult et al. |

FOREIGN PATENT DOCUMENTS

FR  1 563 868 A  4/1969

* cited by examiner

*Primary Examiner* — Nikita Wells
(74) *Attorney, Agent, or Firm* — Michael C. Staggs

(57) ABSTRACT

The embodiments of the present invention are directed to addressing the complexity, sample geometry, and even pressure feedback issues associated with mechanical-only mechanisms. In particular, by utilizing one or more bellows capsules in an attenuated total internal reflection (ATR) instrument as a pressure vessel that can expand, contract, and tilt in all directions, the mechanisms disclosed herein can substantially apply uniform pressure to an interposed sample surface to include non-orthogonal sample surfaces, and thus conform to any sample geometry within such instruments. The result of the novel arrangements described herein is to provide a user with a convenient and simple interface for operating the interrogating ATR optical instrument.

10 Claims, 3 Drawing Sheets

BELLOWS ACTUATED INFRARED (IR) STAGE

CROSS-REFERENCE TO RELATED APPLICATIONS

This application claims the priority benefit under 35 U.S.C. §119(e) of U.S. provisional patent application 61/475,545 for "Bellows Actuated Infrared (IR) Stage", filed Apr. 14, 2011, the entire disclosure of which is incorporated herein by reference.

BACKGROUND OF THE INVENTION

1. Field of the Invention

The present invention relates to spectroscopy and more specifically, the present invention relates to a system and method for beneficially coupling a sample and an internally reflecting element (IRE) within an attenuated total internal reflection (ATR) microscope.

2. Description of Related Art

Attenuated total reflectance (ATR) is an optical interrogation technique often used in conjunction with infrared spectroscopy, which enables samples to be examined directly in a solid, liquid or a gas state. In particular, ATR capitalizes on total internal reflected light produced at the interface of a configured internally reflecting element (IRE) and a coupled sample plane. In operation, a beam of light (e.g., infrared) is passed through the IRE crystal in such a way that it reflects at least once off the internal surface in contact with the sample. This reflection forms an evanescent wave which extends into the sample, often up to about 2 microns, with the exact value being determined by the wavelength of light, the angle of incidence and the indices of refraction for the IRE crystal and the sample medium being interrogated. The reflected beam, which carries the spectral information of the sample, is thereafter interrogated for analysis via, for example, a linear or 2 dimensional array detector.

As generally alluded to above, the samples (e.g., in solid form) to be interrogated using ATR as the investigation technique can come in the form of many different shapes and sizes as the desired samples are often cut, dissected, and polished for molecular analysis. Such mechanical preparation thus often provides rough and often unorthodox shapes that nonetheless still require being efficiently optically coupled between a diamond, silicon, or Germanium (Ge) crystal and a configured stage mechanism that embodies the heart of the microscope system.

In particular, the utilized high index crystal material, which is transparent to the interrogating beam, also provides for a configured hard surface (e.g., a concave, convex, beveled, but often flat surface) to enable compressive forces to be applied to such a configured surface(s) and a mechanical mechanism that introduces the sample. Therefore, a pressure mechanism is required to compress the sample tightly against the desired crystal surface but since the sample geometry is never truly orthogonal to the beam axis, the actual compression pressure varies across the sample area that is being interrogated.

Accordingly, by providing uneven pressure (e.g., for imaging ATR applications) over the interrogated sample area can result in a variation in the return signal strength and thus can degrade the desired spectral information. In addition, because samples can vary in density and hardness, (e.g., a powder sample may provide good results when compressed as opposed to a harder material that maintains its shape under compression) providing efficient compressive coupling between the stage mechanism and the sample surface geometry is desired in order to also not affect the investigating signal strength.

Conventional stages that encounter such signal strength problems discussed above, in addition to other mechanically induced deleterious effects, include mechanical screws, levers, slides, and actuators that are designed to apply desired compressive forces on a given sample. However, such mechanisms are complex, require frequent maintenance, require tight tolerances, and often only apply forces only along a single directional axis. Accordingly, the present invention is directed to addressing the complexity, sample geometry, in addition to feedback issues associated with such mechanical-only mechanisms.

SUMMARY OF THE INVENTION

An aspect of the present invention is to provide an attenuated total internal reflection (ATR) compression apparatus that includes: a disposed optical material; an internally reflecting optical element (IRE) having a contact area configured to receive the disposed optical material; a first adjustable diaphragm mechanically coupled to the disposed optical material; a second adjustable diaphragm sealably coupled to the first adjustable diaphragm; pressurizing means for creating a desired pressure within the second adjustable diaphragm so as to enable movement of the first adjustable diaphragm in a predetermined manner that provides conformable contact of the disposed optical material with the contact area of the internally reflecting optical element (IRE).

Accordingly, the embodiments disclosed herein provide for a bellows actuated infrared (IR) optical measurement instrument that eliminates the need for mechanical pressure towers. In particular, the bellows arrangements disclosed herein are designed to substantially apply uniform pressure to an interposed sample surface to include non-orthogonal sample surfaces, and thus conform to any sample geometry within such instruments.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
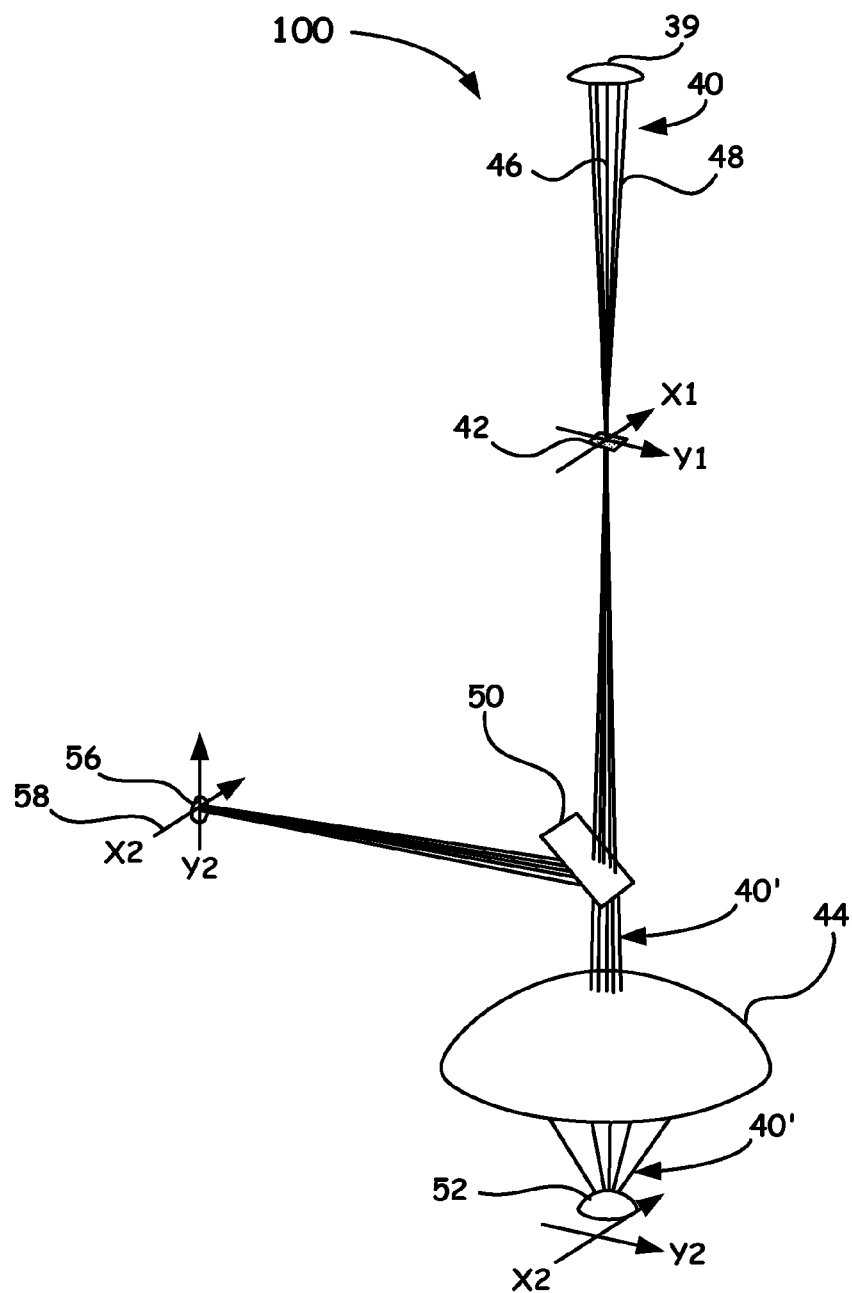
FIG. 1 shows a schematic representation of an ATR microscope capable of being configured with a bellows IR stage as disclosed herein.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

As stated above, the example embodiments described herein are directed to addressing the complexity, sample geometry, and even pressure feedback issues associated with mechanical-only mechanisms. In particular, the embodiments of the present invention utilize one or more bellows capsules as a pressure vessel that can expand, contract, and tilt in all directions so as to substantially apply uniform pressure on a sample surface, even on non-orthogonal sample surfaces, and thus conform to any sample geometry. By arranging the bellows as an example preferred dual configuration (one bellows compressing the sample while the other provides for control) enables a user friendly convenient and simple interface for operating the ATR instrument.

In essence, the example embodiments of the present invention address how samples (e.g., compounds) are compressed for infrared (IR) ATR analysis. Rather than utilizing drive screws, levers, and wedges to create pressure on a medium, the example embodiments herein utilize one or more bellows, the benefit of which is its ability to expand and contract in a novel configured manner. Beneficially, since the constructed structures are often, but not necessarily, round in cross-section, the coupled bellows endplate (e.g. a removable sample carrier) can tilt in all directions so as to align with the sample (s) surface during compression. Such an arrangement is a desired feature since the pressure is thus applied evenly across a given surface, the result of which provides for more consistent spectroscopic sample information.

It is to be appreciated however, that although the preferred embodiment calls out for round structures, the bellows itself can also be of a non-round shape. Moreover, the bellows can be constructed from a number of materials, such as, metal (e.g., steel, stainless steel, alloys, etc.) and even non metals such as, but not limited to, urethane, composites, plastics, or even rubber as long as long the pressure and surrounding environment does not break the material down while in operation. In addition, such bellows can be provided by processes that includes molding, stamping, thermo-forming, etc., as known to those of ordinary skill in the art.

Specific Description

FIG. 1 is provided to illustrate to the reader the overall workings of an ATR instrument, as generally referenced by the numeral 100. However, it is to be understood that the bellows configuration is not solely limited to such instruments as shown in FIG. 1 as the pressure mechanism is adaptable to a variety of instruments that can benefit from automated pressure analysis to obtain, as one prime example, the best signal to noise ratio for infrared measurements. Moreover, while such instrument is shown in a reflective geometry, it is to be understood that while not directly shown, the instruments described herein can also be utilized in a transmissive mode of operation when reconfigured, although such an arrangement is not necessary for the understanding of the novel embodiments of the present invention. Turning back to the discussion of FIG. 1, a focused beam 40, configured from one or more optical components 39, is provided from an optical source (not shown), that is often an infrared energy source. While an infrared energy source is the preferred arrangement, it is to be also understood that the configurations disclosed herein can also be coupled with optical sources that can provide a myriad of wavelengths and corresponding amounts of desired intensities ranging from the ultraviolet through the visible as well as the near-infrared, mid-infrared, and even up to the far-infrared regime. While a large number of rays are utilized, only 5 example rays of the focused beam 40 are shown for simplicity and ease of reading. The beam illuminates a desired area at the "field" plane 42 (also shown with imaging directional arrows labeled x1 and y1). This is also the back focal plane of an optical element, in this case, a Schwarzschild objective 44. Two sets of exemplary rays are labeled, wherein ray 46 is incident at the center of the field plane and ray 48 is incident at an edge.

Half of the focused beam 40' passes an interposed directional mirror 50, and is focused by the Schwarzschild objective 44 to a sample (not shown) configured at a sample plane denoted as x2, y2, that is in placed in intimate contact with the bottom of, for example, a germanium hemisphere 52 operating as the IRE. The overall magnification of the system from the field plane 42 to the sample is up to about fourfold, i.e., by a factor roughly equal to the refractive index of the utilized IRE crystal, i.e., (Ge) at wavelengths of interest. It is to be appreciated that while germanium (Ge) is utilized for the discussion, it is to be also noted that other materials used as the internally reflecting element (IRE) can also be integrated when and if desired without departing from the spirit and scope of the embodiments disclosed herein. For example, materials for ATR crystals can also include, KRS-5 and zinc selenide, silicon for the Far-IR region of the electromagnetic spectrum, and even diamond when studying very hard solids although such a material is costly. In addition, the shape of the crystal can vary (e.g., hemispherical, cylindrical, square, rectangular, etc.) especially when the nature of the sample calls for such varying shapes.

Turing back to FIG. 1, due to the symmetry of the system, rays that reflect from the interface between the germanium hemisphere 52 and a sample (not shown) situated at plane x2, y2, are imaged to a detector plane 56 (now shown with the imaging directional arrows rotated but again labeled x2, y2, with the same magnification factors involved, i.e., about a 1:1 imaging between the field plane 42 and the detector plane 56. A detector (not shown) at detector plane 56 can often be configured as a linear array of elements, oriented along the x axis (i.e., the arrow labeled 58 with respect to the detector plane 56) so as to investigate the return spectral information.

Figure 2:
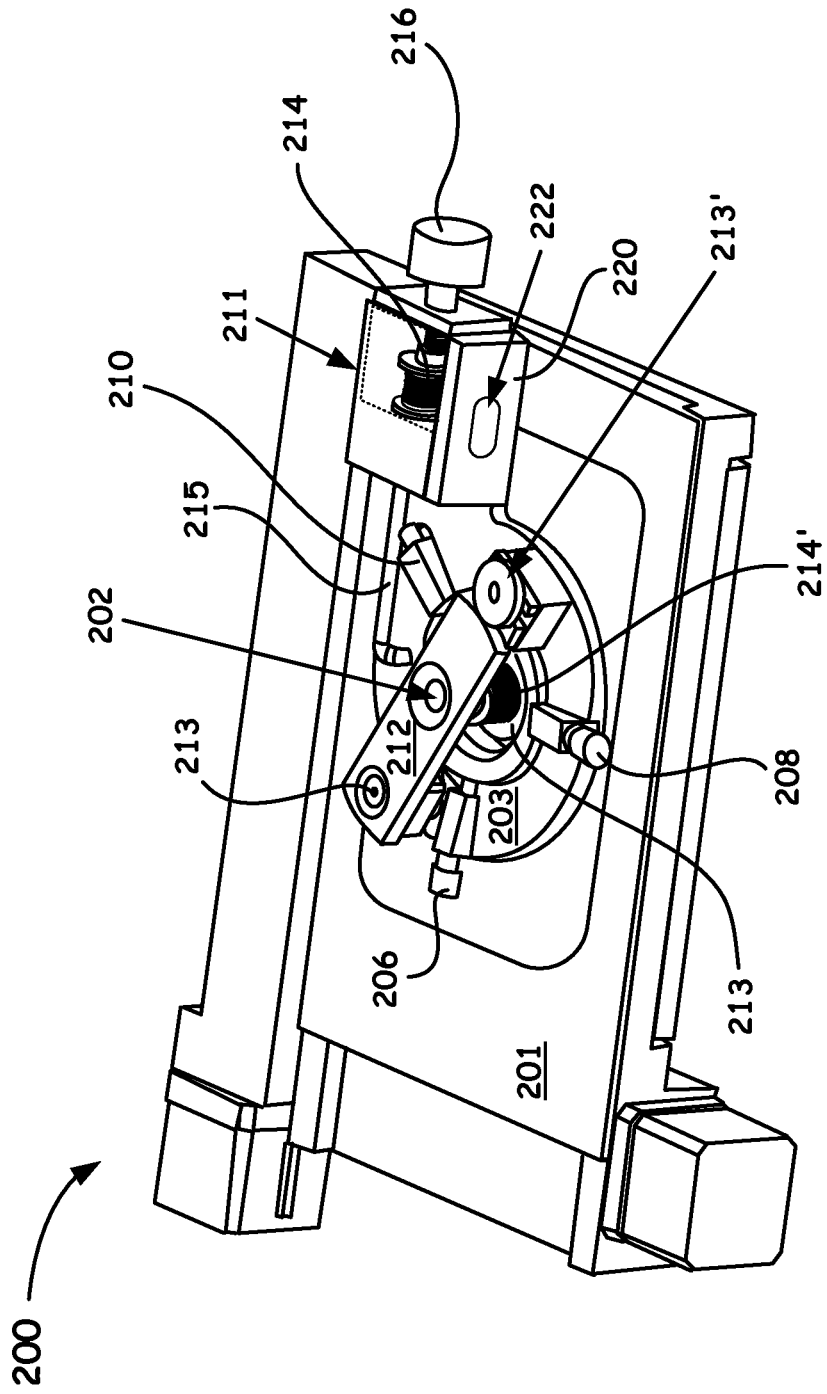
FIG. 2 shows an example bellows IR stage embodiment of the present invention.

FIG. 2 shows a general example configuration at the heart of the invention, i.e., the bellows actuated stage, which is now generally referenced by the apparatus numeral 200. FIG. 2 thus generally shows the stage having a number of parts that hold, manipulate, monitor, etc., the stage 200, of which often includes a microscope stage 201, an IRE optical element 202 (e.g., Ge), a pair of adjustable X, Y, adjusters 206, 208 so as to manipulate a sub-stage 203 (often constructed of material to provide magnetic hold-down) as pressed against a spring force means 210. Apparatus 200 also comprises a control bellows assembly 211, a distal flexible diaphragm (hereinafter sample bellows 214'), a lever arm 212 (having a pivoting means 213 (rod) and a locking means 213' (e.g., knob and notch receiver), pneumatic or hydraulic coupling means 215, and a pressure sensor 220 (e.g., a digital pressure sensor) having a viewing window 222 to monitor, for example, a digital representation (i.e., an LCD display) of the fluid pressure being applied to a given sample (not shown).

Figure 3A:
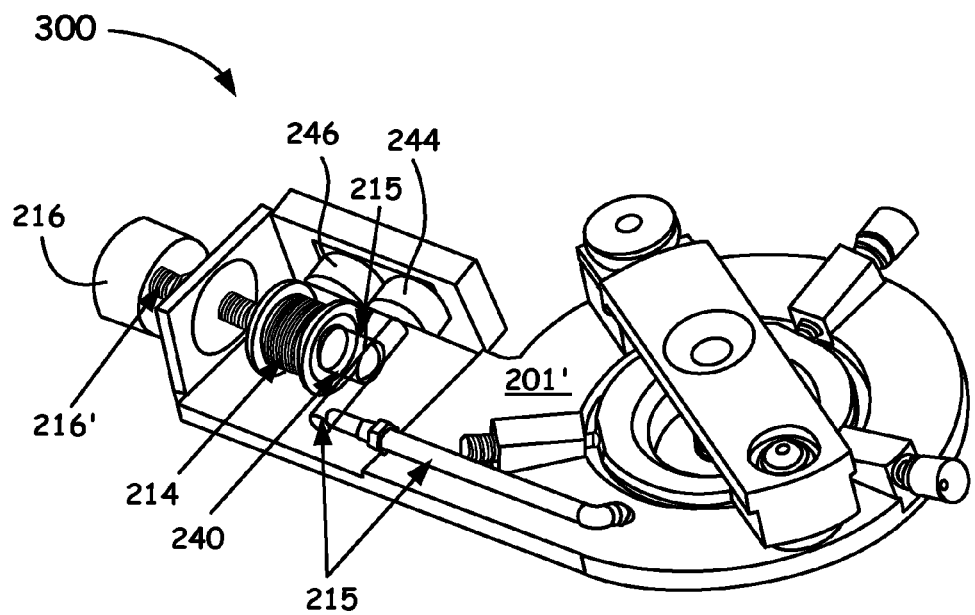
FIG. 3A shows a perspective view of a portion of an ATR IR stage to better illustrate the control bellows pressure arrangement disclosed herein.
Figure 3B:
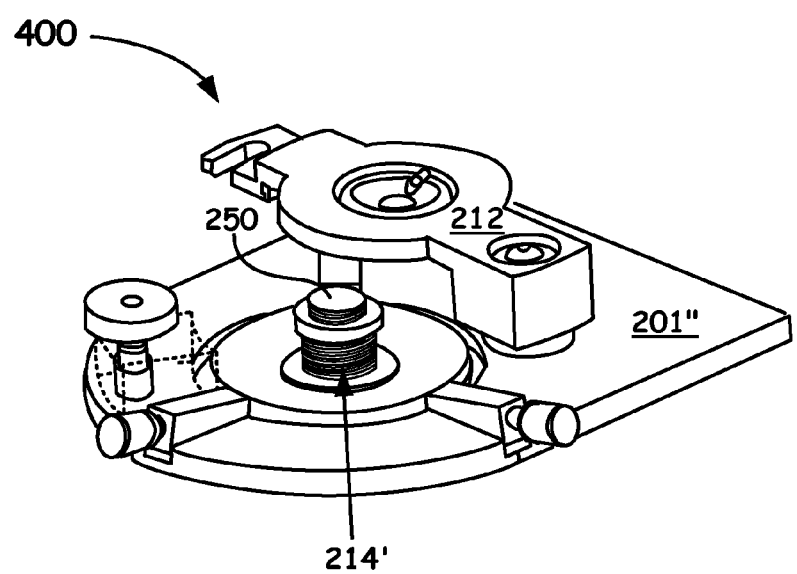
FIG. 3B shows another different perspective view of a portion of an example ATR IR stage to better illustrate the sample bellows pressure arrangement.

In operation, a desired sample (not shown) is often but not necessarily disposed on a sample plate (see reference character 250 of FIG. 3B). The IRE 202 (having a sample contact area of up to about 5 mm, preferably up to about 2 mm) is thereafter configured to be removably put into alignment and proximate contact with the sample (not shown) using elements of lever arm 212 (i.e., pivoting means 213 and locking means 213') and if required, adjustable X, Y, adjusters 206, 208. To provide intimate (conformable) contact of the sample and IRE 202, a controlled pressure of up to about 3300 psi is provided by a proximate flexible diaphragm (hereinafter control bellows 214, as shown within the dashed cutaway of assembly 211). Along with coupling means 215, control bellows 214 is filled with a fluid (e.g., a gas but preferably a liquid, such as, but not limited to oil) in a closed loop operation (to include the coupled pressure sensor 220) to a predetermined level to enable actuation when provided with a force via, for example an automatic (not shown) or manual mechanical means 216 (e.g., knob).

Using a knob 216 for purposes of the discussion, as knob 216 (having a mated threading with assembly 211 or configured as a pull/push design for controlled manipulation) is utilized to compress control bellows 214, the pressure developed within control bellows 214 rises to direct the contained fluid in a desired laminar and/or turbulent fashion to coupling means 215. Correspondingly, the pressure rises within coupling means 215 as based upon Pascal's law. Such an example arrangement can desirably enable a controlled compression to a load, i.e., a sample plate (not shown) disposed on a distal end of coupling means 215. A sample (also not shown) residing on such a plate is thus substantially placed in uniform contact to the back face of the configured IRE 202 via the desired pressure applied and as monitored using the LCD readout 222 of pressure sensor 220. To reverse the process, knob 216 is moved in the counter direction expanding control bellows 214 so as to reduce pressure and decouple a chosen sample from a particular IRE 202.

It is to be appreciated that while not shown, the configurations discussed above and hereinafter also include pressure seals (often with no dynamic sliding seals) to contain the disposed fluid and pressure release valves to limit unwanted pressures that can result in system failure. In addition, the configured pressure sensor 220, (e.g., transducers, piezoelectric sensors, etc., of known construction) can also be internally constructed with a flexure (e.g., a spring) to adjust and/or calibrate applied pressures of the system to the desired pressure ranges.

While such an arrangement is beneficial, the apparatus 200 of FIG. 2 is more often arranged with a plurality of bellows. Preferably, the apparatus 200 of FIG. 2 is configured solely with only two bellows, i.e., a control bellows 214 as discussed above, and a sample bellows 214' coupled to the distal end of coupling means 215 and disposed therebetween but coupled to the sample plate (250 of FIG. 3B). It is to be appreciated that the described bellows herein can be thin-walled but of sufficient thickness and pleated to form convolutions for expansion and compression movements. To provide such configurations, the bellows described herein are capable of being constructed from known processes and from a number of materials, such as, metal (e.g., steel, stainless steel, alloys, etc.) and even non metals such as, but not limited to, urethane, composites, plastics, or even rubber as long as long the pressure and surrounding environment does not break the material down while in operation.

Moreover, while the flexible diaphragms itself (i.e., bellows) are preferably constructed from metal, such as for, example steel, the bellows nonetheless notably comprise a capsule of diaphragms to provide the pleated arrangement wherein the total stroke of the bellows (e.g., sample bellows 214') is limited only by such capsules and wherein even in compression, the designed capsules do not interfere with adjacent capsules so as to deteriorate any part of the overall diaphragm construction. It is also to be noted that the sample bellows 214' configuration is designed to preferably provide up to about 9 millimeters (mm) of travel and even more preferably at least up to about 5-6 mm of travel along an interrogation axis of the microscope of FIG. 1. In addition, it is to be also noted that the top plurality of capsules (at least two) of the designed capsules are designed, where desired, to be configurably open so as to beneficially aid (in addition to the round structure) conformable X, Y tilt of the coupled sample plate (see reference character 250 of FIG. 3B) to provide the intimate (conformable) contact of IRE 202 and a sample (not shown) that often can even be irregularly shaped.

In operation of this beneficial but preferred arrangement, a desired sample (not shown) is again capable of being disposed on sample plate (see reference character 250 of FIG. 3B) and the IRE 202 (having a sample contact area of up to about 5 mm, preferably up to about 2 mm) is again thereafter configured to be removably put into alignment and proximate contact with the sample using elements of lever 212 as discussed above, and if required, adjustable X, Y, adjusters 206, 208. The intimate contact of the sample and IRE 202 as enabled by a controlled pressure of up to about 3300 psi is again provided by an actuated control bellows 214 that in addition to coupled sample bellows 214' and coupling means 215 is filled in a closed loop operation (again to include the coupled pressure sensor 220) to a predetermined level with a fluid as disclosed above. As before, actuation of the bellows design is provided by the forced movement of mechanical means 216. In particular, as knob 216 is utilized to compress control bellows 214, the pressure developed within control bellows 214 rises to direct the contained fluid in a desired laminar and/or turbulent fashion to coupling means 215 so as to now beneficially expand sample bellows 214' via Pascal's law, of which provides the desired pressurized contact of the sample and the sample contact area of the IRE 202. A sample (not shown) residing on plate (250 of FIG. 3B) is thus substantially placed in uniform (conformable) contact to the back face of the configured IRE 202 via the desired pressure applied and as monitored using the LCD readout 222 of pressure sensor 220. Retraction is enabled by reversing the steps as discussed above.

FIG. 3A, now referenced generally by the numeral 300, shows a perspective view of a portion of ATR IR stage 201' to give the reader a deeper appreciation of the novel control bellows 214 pressure arrangement, as shown generally by the assembly 211 of FIG. 2. In particular, FIG. 3A shows the control bellows, as discussed above, as coupled to mechanical means, e.g., knob 216 having when desired, a threaded capability 216' (e.g., ¼-20, ¼-28 threads, etc.). Such an arrangement enables compression of bellows 214 using a configured ball end (not shown) of the threaded portion of knob 216 to drive inward and expansion of control bellows 214 when knob 216 is manipulated in the reverse manner. Also of note is the plumbing of coupling means 215 with respect to plate 201' and the coupled (often hydraulically coupled) pressure transducer 244. Upon actuation of the system(s) disclosed herein, as discussed above, such a transducer 244 provides a readout of the monitored desired pressure induced to the bellow(s) via the electrically coupled LCD display (not shown) as powered by, for example, an adjacently coupled source 246, (battery).

FIG. 3B, now referenced generally by the numeral 400, shows an even simpler perspective variation embodiment of a portion of ATR IR stage 201" so as to illustrate the sample bellows 214' pressure arrangement, as discussed above. In particular, FIG. 3B shows a beneficial sample bellows 214' as coupled to sample plate 250, as discussed above, now shown in a configuration ready to receive a sample (not shown) by way of the lever arm 212 being unlocked and put into an open position.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. An attenuated total internal reflection (ATR) compression apparatus, comprising:
   a disposed optical material;
   an internally reflecting optical element (IRE) having a contact area configured to receive said disposed optical material;
   a first adjustable diaphragm mechanically coupled to said disposed optical material;
   a second adjustable diaphragm sealably coupled to said first adjustable diaphragm;
   pressurizing means for creating a desired pressure within said second adjustable diaphragm so as to enable movement of said first adjustable diaphragm in a predetermined manner that provides conformable contact of said disposed optical material with said contact area of said internally reflecting optical element (IRE).

2. The apparatus of claim 1, wherein said pressurizing means further comprises oil utilized as a hydraulic fluid for pressurizing said first adjustable diaphragm.

3. The apparatus of claim 1, wherein said first adjustable diaphragm and said second adjustable diaphragm comprises a bellows constructed from at least one material selected from: metal, plastic, urethane, and rubber.

4. The apparatus of claim 3, wherein said bellows comprises a plurality of capsules.

5. The apparatus of claim 3, wherein a plurality of capsules configured at the top of said bellows are further configured for X, Y tilt capability.

6. The apparatus of claim 1, wherein said desired pressure is monitored by a coupled pressure transducer.

7. The apparatus of claim 6, wherein said desired pressure as monitored by said coupled pressure transducer is configured with an internal spring to adjust and/or calibrate applied pressures of the system to said desired pressures.

8. The apparatus of claim 1, wherein said first adjustable diaphragm is configured to provide up to 9 millimeters of travel along a desired axis.

9. The apparatus of claim 1, wherein said internally reflecting optical element (IRE) is selected from at least one material selected from: Germanium (Ge), KRS-5, zinc selenide, silicon, and diamond.

10. The apparatus of claim 9, wherein said internally reflecting optical element (IRE) is configured with at least one shape selected from: hemispherical, cylindrical, square, and rectangular.

* * * * *